(12) United States Patent
Carlson et al.

(10) Patent No.: US 11,696,782 B2
(45) Date of Patent: Jul. 11, 2023

(54) ROTATIONAL MEDICAL DEVICE

(71) Applicant: BOSTON SCIENTIFIC SCIMED, INC., Maple Grove, MN (US)

(72) Inventors: Corydon Carlson, Stillwater, MN (US); David Gordon Spangler, New Richmond, WI (US); Daniel Frank Massimini, Brooklyn Park, MN (US); Laszlo Trent Farago, Hudson, WI (US); Mark A. Hilse, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 341 days.

(21) Appl. No.: 16/217,009

(22) Filed: Dec. 11, 2018

(65) Prior Publication Data

US 2019/0175211 A1    Jun. 13, 2019

Related U.S. Application Data

(60) Provisional application No. 62/597,721, filed on Dec. 12, 2017.

(51) Int. Cl.
*A61B 17/32* (2006.01)
*A61B 17/3207* (2006.01)
(Continued)

(52) U.S. Cl.
CPC .. *A61B 17/320758* (2013.01); *A61B 1/00133* (2013.01); *A61B 17/00234* (2013.01);
(Continued)

(58) Field of Classification Search
CPC ........... G05B 2219/41092; G05B 2219/49382; G05B 2219/35455; G05B 2219/45118;
(Continued)

(56) References Cited

U.S. PATENT DOCUMENTS

| 5,270,622 A | 12/1993 | Krause |
| 5,602,449 A * | 2/1997 | Krause ................ H02H 7/0822 |
| | | 318/400.11 |

(Continued)

FOREIGN PATENT DOCUMENTS

| AU | 2017204839 A1 | 8/2017 |
| EP | 0649217 A1 | 4/1995 |

(Continued)

OTHER PUBLICATIONS

International Search Report and Written Opinion dated Mar. 13, 2019 for International Application No. PCT/US2018/065048.

*Primary Examiner* — Rina I Duda
(74) *Attorney, Agent, or Firm* — Seager, Tufte & Wickhem LLP

(57) ABSTRACT

Medical systems and methods for making and using medical systems are disclosed. Example medical systems may include an atherectomy system configured to engage and remove plaque from walls in vessels of a vascular system. The atherectomy system may include a drive shaft, a rotational member coupled to an end of the drive shaft, a motor coupled to the drive shaft to rotate the rotational tip, and a control unit configured to control a motor state of the motor. The motor may be an electric motor. The control unit may adjust the motor state to decelerate the motor in response to detecting a jam or a stall condition. The jam or stall condition may be detected when a speed of the motor or other motor state reaches or goes beyond a threshold value as prescribed by a reference schedule.

19 Claims, 8 Drawing Sheets

(51) Int. Cl.
*A61B 1/00* (2006.01)
*A61B 17/00* (2006.01)
*G05B 19/4061* (2006.01)
*A61B 90/00* (2016.01)

(52) U.S. Cl.
CPC .... *A61B 17/32002* (2013.01); *G05B 19/4061* (2013.01); *A61B 2017/00017* (2013.01); *A61B 2017/00398* (2013.01); *A61B 2090/031* (2016.02); *G05B 2219/37622* (2013.01); *G05B 2219/42325* (2013.01)

(58) Field of Classification Search
CPC ....... G05B 19/404; G05B 19/232; H02P 6/16; H02P 6/24
See application file for complete search history.

(56) References Cited

U.S. PATENT DOCUMENTS

| | | | |
|---|---|---|---|
| 5,672,945 A | 9/1997 | Krause | |
| 5,972,012 A * | 10/1999 | Ream | A61B 17/32002 604/22 |
| 6,015,420 A | 1/2000 | Wulfman et al. | |
| 6,206,898 B1 * | 3/2001 | Honeycutt | A61B 17/320758 606/159 |
| 6,596,005 B1 | 7/2003 | Kanz et al. | |
| 7,174,240 B2 | 2/2007 | Shturman et al. | |
| 7,584,022 B2 | 9/2009 | Shturman et al. | |
| 7,862,575 B2 * | 1/2011 | Tai | A61B 17/00008 606/159 |
| 7,967,834 B2 * | 6/2011 | Tai | A61B 17/320758 606/159 |
| 7,982,425 B2 * | 7/2011 | Minamide | G05B 19/404 318/280 |
| 8,657,821 B2 * | 2/2014 | Palermo | A61B 17/320758 606/80 |
| 9,050,123 B2 * | 6/2015 | Krause | A61B 17/32002 |
| 9,050,126 B2 | 6/2015 | Rivers et al. | |
| 9,119,660 B2 | 9/2015 | Rivers et al. | |
| 9,119,661 B2 | 9/2015 | Rivers et al. | |
| 9,220,529 B2 | 12/2015 | Rivers et al. | |
| 9,265,585 B2 * | 2/2016 | Wingardner | A61B 17/07207 |
| 2005/0042572 A1 * | 2/2005 | Katsuda | A61C 1/0015 433/98 |
| 2010/0125276 A1 | 5/2010 | Palermo | |
| 2012/0130410 A1 * | 5/2012 | Tai | A61B 17/320758 606/159 |
| 2013/0018398 A1 | 1/2013 | Rivers et al. | |
| 2013/0321262 A1 * | 12/2013 | Schecter | G06F 3/041 345/156 |
| 2014/0364883 A1 | 12/2014 | Schoenle et al. | |
| 2014/0365691 A1 | 12/2014 | Schoenle et al. | |
| 2014/0371770 A1 | 12/2014 | Schoenle et al. | |
| 2015/0051626 A1 | 2/2015 | Rivers et al. | |
| 2016/0354108 A1 * | 12/2016 | Nakano | A61B 17/320758 |
| 2016/0374716 A1 * | 12/2016 | Kessler | A61B 17/22031 606/159 |

FOREIGN PATENT DOCUMENTS

| | | |
|---|---|---|
| JP | 2014500761 A | 1/2014 |
| JP | 2016221081 A | 12/2016 |

\* cited by examiner

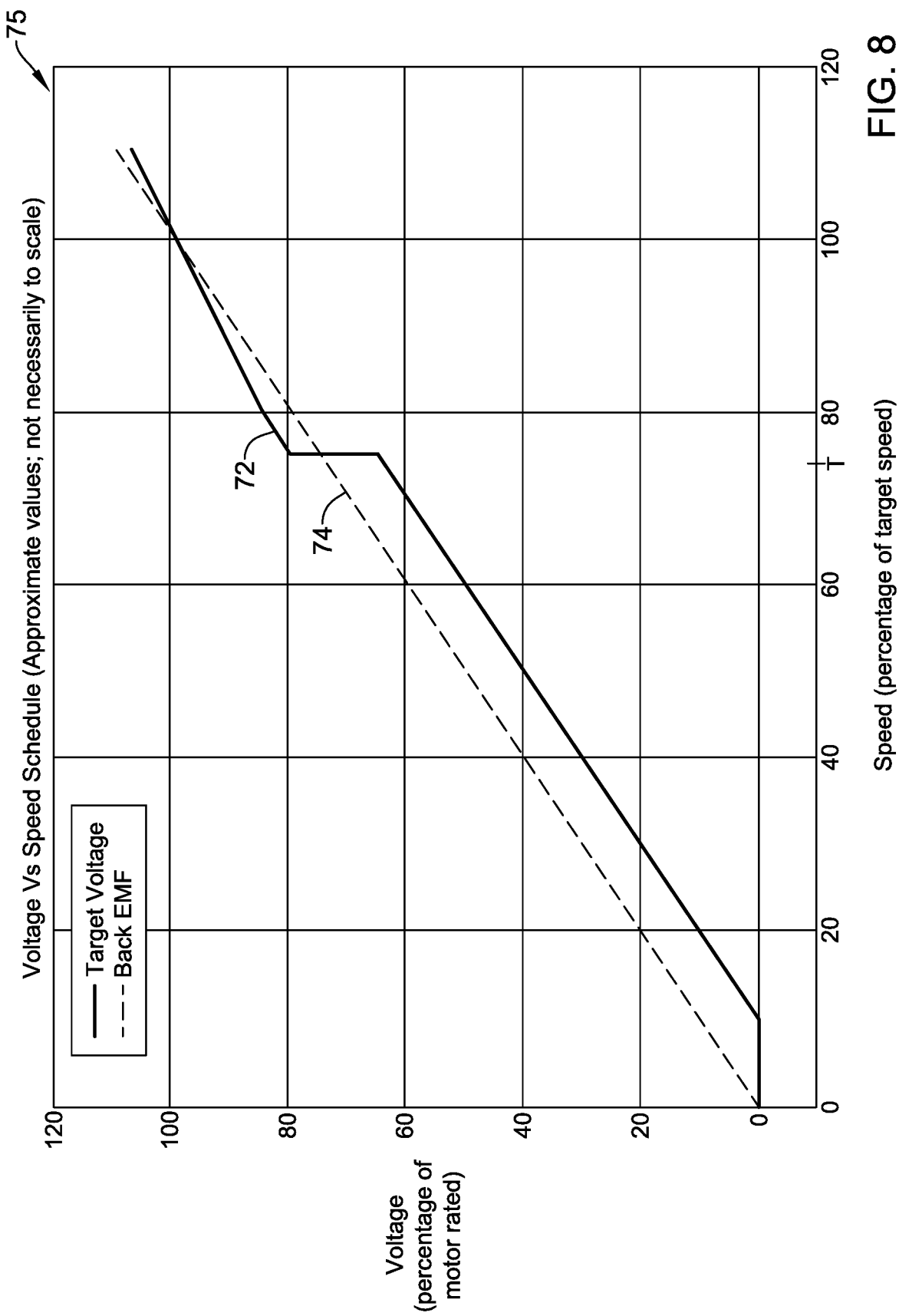

ROTATIONAL MEDICAL DEVICE

CROSS-REFERENCE TO RELATED APPLICATIONS

This application claims the benefit of priority under 35 U.S.C. § 119 of U.S. Provisional Application No. 62/597,721, filed Dec. 12, 2017, the entire disclosure of which is hereby incorporated by reference.

TECHNICAL FIELD

The present disclosure pertains to medical devices, and methods for manufacturing and using medical devices. More particularly, the present disclosure pertains to rotational medical devices, methods, and systems, including those with electric motors.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

BRIEF SUMMARY

This disclosure provides, design, material, manufacturing method, and use alternatives for medical devices and systems. In a first aspect, a medical device may comprise a drive shaft, a rotational member coupled to a first end of the drive shaft, a motor coupled to a second end of the drive shaft to rotate the rotational tip, and a control unit configured to control a motor state of the motor, the control unit is further configured to adjust the motor state to decelerate the motor in response to a detected stall condition.

In addition or alternative and in a second aspect, the motor state may be a torque on the motor, and the stall condition may be detected when a speed of the motor reaches or goes beyond a threshold level.

In addition or alternative and in a third aspect, adjusting the torque on the motor may include reversing a direction of torque on the motor.

In addition or alternative and in a fourth aspect, the control unit may be configured to adjust the motor state of the motor by reversing a direction of current provided to the motor to decelerate the motor in response to the detected stall condition.

In addition or alternative and in a fifth aspect, the control unit may be configured to adjust the motor state of the motor by reducing an amount of voltage provided to the motor to decelerate the motor in response to the detected stall condition.

In addition or alternative and in a sixth aspect, the control unit may be configured to adjust the motor state of the motor based on a predetermined motor speed reference schedule and motor parameters received by the control unit during operation of the motor.

In addition or alternative and in a seventh aspect, the motor parameters may include a measurement of current provided to the motor and a measurement of a rotational position of the motor.

In addition or alternative and in an eighth aspect, the medical device may further include a first sensor sensing a current provided to the motor, a second sensor sensing a position of the motor, and the first sensor may provide a signal indicative of a sensed current to the control unit and the second sensor may provide a signal indicative of a sensed position to the control unit.

In addition or alternative and in a ninth aspect, the control unit may be configured to determine a speed of the motor based on the signal indicative of a sensed position of the motor, and the control unit may be configured to determine the motor state of the motor based on the signal indicative of a sensed current and the signal indicative of a sensed position, the determined motor state may be a motor state other than the determined speed of the motor.

In addition or alternative and in a tenth aspect, the control unit may be configured to determine a reference motor state based on the speed of the motor and compare the determined reference motor state to the determined motor state, and issue a command signal for the motor based on the comparison between the reference motor state to the determined motor state.

In addition or alternative and in an eleventh aspect, a control unit may comprise a controller, a motor state estimator in communication with the controller, and a reference schedule component in communication with the controller and the motor state estimator, the reference schedule component is configured to provide an output to the controller based on an input from the motor state estimator, and wherein the controller may be configured to output a control signal for decelerating a motor based on the output received from the reference schedule component when the input to the reference schedule component from the motor state estimator reaches or goes beyond a threshold level.

In addition or alternative and in a twelfth aspect, the input to the reference schedule component from the motor state estimator may be a motor speed and the reference schedule component may be configured to provide a reference motor state based on the motor speed.

In addition or alternative and in a thirteenth aspect, the motor state estimator may be configured to receive signals indicative of sensed motor parameters and provide an output to the controller based on the received signals indicative of sensed motor parameters, and the outputted control signal may be based on the output from the motor state estimator to the controller.

In addition or alternative and in a fourteenth aspect, the output from the reference schedule component to the controller may be a reference motor state and the output from the motor state estimator to the controller may be a real time motor state, and the controller may be configured to determine the control signal based on a difference between the reference motor state and a real time motor state.

In addition or alternative and in a fifteenth aspect, the reference motor state may be a reference torque for the motor and the real time motor state may be a real time torque of the motor.

In addition or alternative and in a sixteenth aspect, the control unit may further include a processor, memory in communication with the processor, and an input/output port in communication with the processor, and wherein the processor and the memory may be configured to effect operation of the controller and the reference schedule component to output the control signal via the input/output port.

In addition or alternative and in a seventeenth aspect, a method of controlling a medical device may include receiving signals indicative of a sensed position of a motor, determining a speed of the motor based on the signals indicative of a sensed position of the motor, identifying a reference motor state based on the determined speed of the motor and a predetermined reference schedule, and outputting a control signal to the motor to decelerate the motor, the outputted control signal may be based on the reference motor state.

In addition or alternative and in an eighteenth aspect, the method may further include receiving signals indicative of a sensed current provided to the motor, determining a real time motor state based on the received signals indicative of a sensed motor parameter and the received signals indicative of a sensed current, wherein the outputted control signal may be based on the real time motor state.

In addition or alternative and in a nineteenth aspect, the reference motor state may be a reference motor torque and the real time motor state may be a real time motor torque.

In addition or alternative and in a twentieth aspect, the control signal to decelerate the motor may be outputted to the motor when the determined speed of the motor reaches or goes beyond a threshold level.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

BRIEF DESCRIPTION

The disclosure may be more completely understood in consideration of the following description of various illustrative embodiments of the disclosure in connection with the accompanying drawings, in which:

FIG. 8 is an example reference schedule of motor speed versus drive voltage for an atherectomy system.

Figure 1:
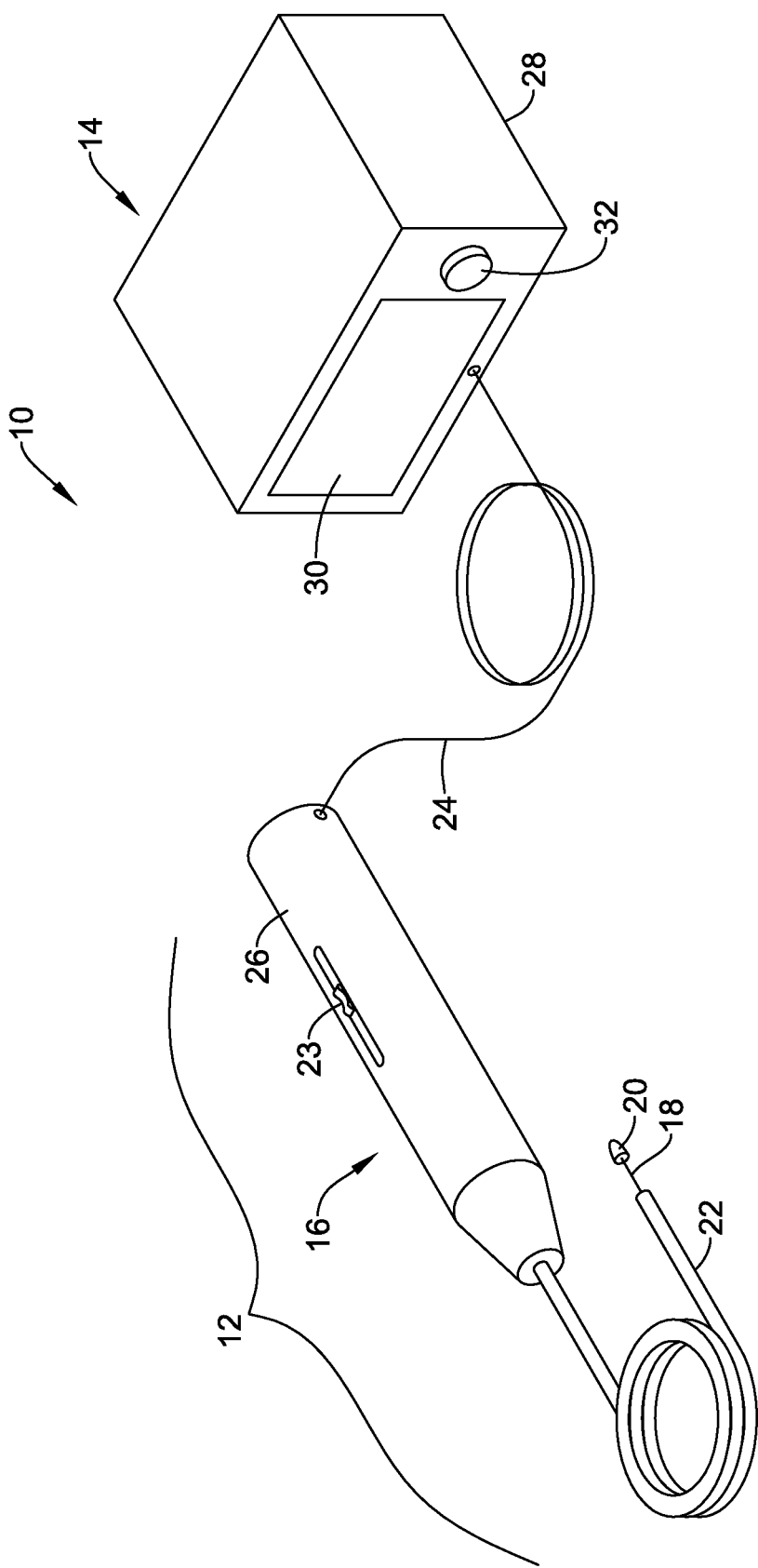
FIG. 1 is a schematic diagram of an example atherectomy system.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described herein. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits restrict blood flow and can cause ischemia in a heart of a patient, vasculature of a patient's extremities (e.g., legs, arms, head, etc.), a patient's carotid artery, and/or in other vasculature of a patient. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and a variety of catheter-based approaches which rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material. In an atherectomy procedure, a device on an end of a drive shaft is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction.

FIG. 1 depicts an atherectomy system 10. The atherectomy system 10 may include a drive assembly 12 and a control unit 14 (e.g., a controller). The drive assembly 12 may include, among other elements, an advancer assembly 16, a drive shaft 18 (e.g., a flexible drive shaft or other drive shaft), a rotational or device 20 (e.g., rotational member such as a rotational tip or other rotational device), and an elongated member 22 having a first end (e.g., a distal end), a second end (e.g., a proximal end), and a lumen extending from the first end to the second end for receiving the drive shaft 18. In some cases, the elongated member 22 may be an elongated tubular member. The rotational device 20 may have a rough, abrasive, or sharp surface, such that it is configured to grind, abrade, cut, shave, etc. plaque from a vessel wall or other obstruction in a vessel when it is rotated.

The advancer assembly 16 may include an advancer knob 23 and may house a motor (e.g., an electric motor, pneumatic motor, or other motor) in communication with the advancer knob 23, the drive shaft 18, and the control unit 14. The advancer knob 23 may be configured to advance along a longitudinal path to longitudinally advance the motor and the rotational device 20. The motor may be coupled to the drive shaft 18 in a suitable manner including, but not limited to, a weld connection, a clamping connection, an adhesive connection, a threaded connection, and/or other suitable connection configured to withstand high rotational speeds and forces. As the drive shaft 18 may rotate over a wide range of speeds (e.g., at speeds of between zero (0) RPM and 250,000 RPM or higher), the coupling between the motor and the drive shaft 18 may be configured to withstand such rotational speeds and associated forces.

The drive shaft 18 may be formed from one or more of a variety of materials. For example, the drive shaft 18 may be formed from one or more of a variety of materials, including steel, stainless steel, and/or other suitable materials.

The drive shaft 18 may have a suitable diameter and/or length for traversing vasculature of a patient. In some cases, the drive shaft 18 may have a diameter in a range from about 0.05 centimeters (cm) to about 0.130 cm and a working length in a range from about ten (10) cm to about two hundred (200) cm. In one example, the drive shaft 18 may have a diameter of about 0.05715 cm and a length of about fifty (50) cm. Alternatively, the drive shaft 18 may have a different suitable diameter and/or different suitable length.

The rotational device 20 may have an outer perimeter which is equal to or larger than a distal diameter of the drive shaft 18 and/or the elongated member 22. Alternatively or in addition, the rotational device 20 may have an outer perimeter which is smaller than a diameter of the drive shaft 18 and/or the elongated member 22. The rotational device 20 may have a symmetric design so that it penetrates equally well in both rotational directions, but this is not required and the rotational device 20 may be configured to penetrate in only one direction. The diameter of the drive shaft 18 may depend on the dimension of the lumen of the elongated member 22 and/or one or more other factors.

The rotational device 20 may be coupled to the drive shaft 18. Where the drive shaft 18 has a first end portion (e.g., a distal end portion) and a second end portion (e.g., a proximal end portion), the rotational device 20 may be coupled to the drive shaft 18 at or near the first end portion. In some cases, the rotational device 20 may be located at or adjacent a terminal end of the first end portion of the drive shaft 18.

The rotational device 20 may be coupled to the drive shaft 18 in any manner. For example, the rotational device 20 may be coupled to the drive shaft 18 with an adhesive connection, a threaded connection, a weld connection, a clamping connection, and/or other suitable connection configured to withstand high rotational speeds and forces. Similar to as discussed above with respect to the connection between the drive shaft 18 and the motor, as the drive shaft 18 and/or the rotational device 20 may rotate at speeds between zero (0) RPM and 250,000 RPM or higher, the coupling between the drive shaft 18 and the rotational device 20 may be configured to withstand such rotational speeds and associated forces.

The drive assembly 12 and the control unit 14 may be in communication and may be located in or may have a same housing and/or located in or have separate housings (e.g., an advancer assembly housing 26 and a control unit housing 28 or other housings). Whether in the same housing or in separate housings, the drive assembly 12 and the control unit 14 may be communication through a wired (e.g., via one or more wires in the electrical connector 24) and/or wireless connection. Wireless connections may be made via one or more communication protocols including, but not limited to, cellular communication, ZigBee, Bluetooth, WiFi, IrDA, dedicated short range communication (DSRC), EnOcean, and/or any other suitable common or proprietary wireless protocol, as desired.

Although not necessarily shown in FIG. 1, the drive assembly 12 may include and/or enclose one or more operational features. For example, among other features, the drive assembly 12 may include a motor, a start/stop button, a control knob configured to advance the rotational device 20, rubber feet, mode selection button(s), a mode start/stop button, control electronics, drive circuitry, etc.

The control unit 14, which may be separate from the drive assembly 12 (e.g., as shown in FIG. 1) or may be included in the drive assembly 12, may include several features. For example, as shown in FIG. 1, the control unit 14 may include a display 30 and a control knob 32 (e.g., a motor speed (e.g., RPM or other speed) adjustment knob or other control knob). Additionally or alternatively, the control unit 14 may include one or more other features for controlling the motor and/or other features of the drive assembly 12 (e.g. one or more motor states of the motor) including, but not limited to, a processor, memory, input/output devices, a speaker, volume control buttons, on/off power supply switch, motor activation switch, a timer, a clock, and/or one or more other features.

In some cases, the control unit 14 may include one or more safety mechanisms for controlling an operation of the atherectomy system 10. In one example of a safety mechanism that may be included in the control unit 14, the control unit 14 may be configured to adjust the motor state to decelerate the motor in response to detecting a jam or stall condition. Example motor states that the control unit 14 may be configured to control include, but are not limited to, motor torque, drive current for the motor, drive voltage to the motor, motor speed, etc. Additionally or alternatively, the control unit 14 may include other safety mechanism for controlling the operation of the atherectomy system 10 and mitigating risks to patients. Although detecting a jam or stall condition is discussed herein as being performed by a controller such as the control unit 14, one or more additional or other alternative components may be configured to detect and/or facilitate detecting the jam or stall condition.

Figure 2:
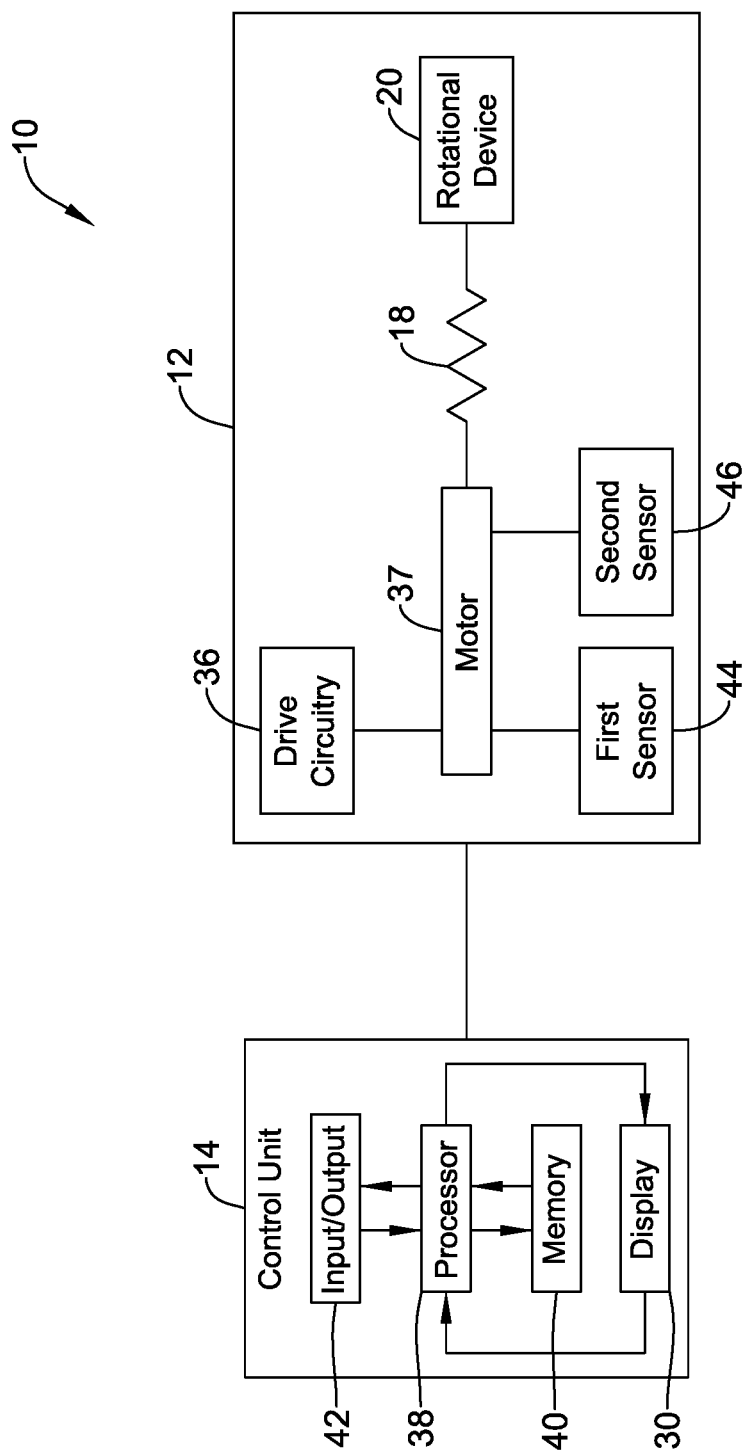
FIG. 2 is a schematic box diagram of an example atherectomy system.

FIG. 2 depicts a block diagram of the atherectomy system 10. Although the drive assembly 12 and the control unit 14 are depicted in FIG. 2 as separate components, an entirety of or portions of the control unit 14 may be incorporated in or with the drive assembly 12 and/or an entirety of or portions of the drive assembly 12 may be incorporated in or with the control unit 14. As discussed above, the drive assembly 12 and the control unit 14 may be in a same housing or separate housings.

The atherectomy system 10 may include drive circuitry 36 (optionally included), a motor 37 (e.g., an electric motor or other suitable drive mechanism) in communication with the drive circuitry 36, sensors (e.g., a first sensor 44, a second sensor 46, and or other suitable sensors) for sensing motor parameters (e.g., drive current, drive voltage, motor position, etc.), and the rotational device 20 in communication with the motor 37 through the drive shaft 18, where the drive assembly 12 is in communication with the control unit 14 over an electrical connection (e.g., the electrical connector 24 or other connection configured to transmit signals). Because torque may build up in the drive shaft 18, the drive shaft 18 is depicted in FIGS. 2 and 3 as a spring.

When the drive circuitry 36 is included in the atherectomy system 10, the drive circuitry 36 may be mounted on a substrate or other component in the advancer assembly housing 26 of the drive assembly 12 and may be in electrical communication with the control unit 14. The drive circuitry 36 may include, but is not required to include, a microprocessor and/or a microcontroller, an application specific integrated circuit ("ASIC"), and/or an application specific standard product ("ASSP"). In some cases, the drive circuitry 36 may be (at least partially) incorporated into the control unit 14, but this is not required.

As discussed above, the control unit 14 may include one or more features configured to facilitate controlling the drive assembly 12. As shown in FIG. 2, the atherectomy system 10 may include (e.g., in the control unit 14 or elsewhere), among other features, a processor 38 (e.g., a microprocessor, a microcontroller, etc.), memory 40, the display 30, and an input/output port 42. The processor 38 may be operatively coupled to the memory 40. The memory 40 may be used to store any desired information, such as control algorithms, set points, schedules, reference schedules, times, diagnostic limits, such as, for example, speed limits, RPM limits, torque limits, current limits, voltage limits, and the like. The memory 40 may include any of one or more suitable types of storage devices including, but not limited to, RAM, ROM, EPROM, flash memory, a hard drive, and/or the like. In some cases, the control unit 14 may store information within the memory 40, and may subsequently retrieve the stored information from the memory 40 to effect operation of the atherectomy device and/or for analysis. Further, the processor 38 and/or the memory 40 may include and/or be in communication with a timer (not shown).

Figure 3:
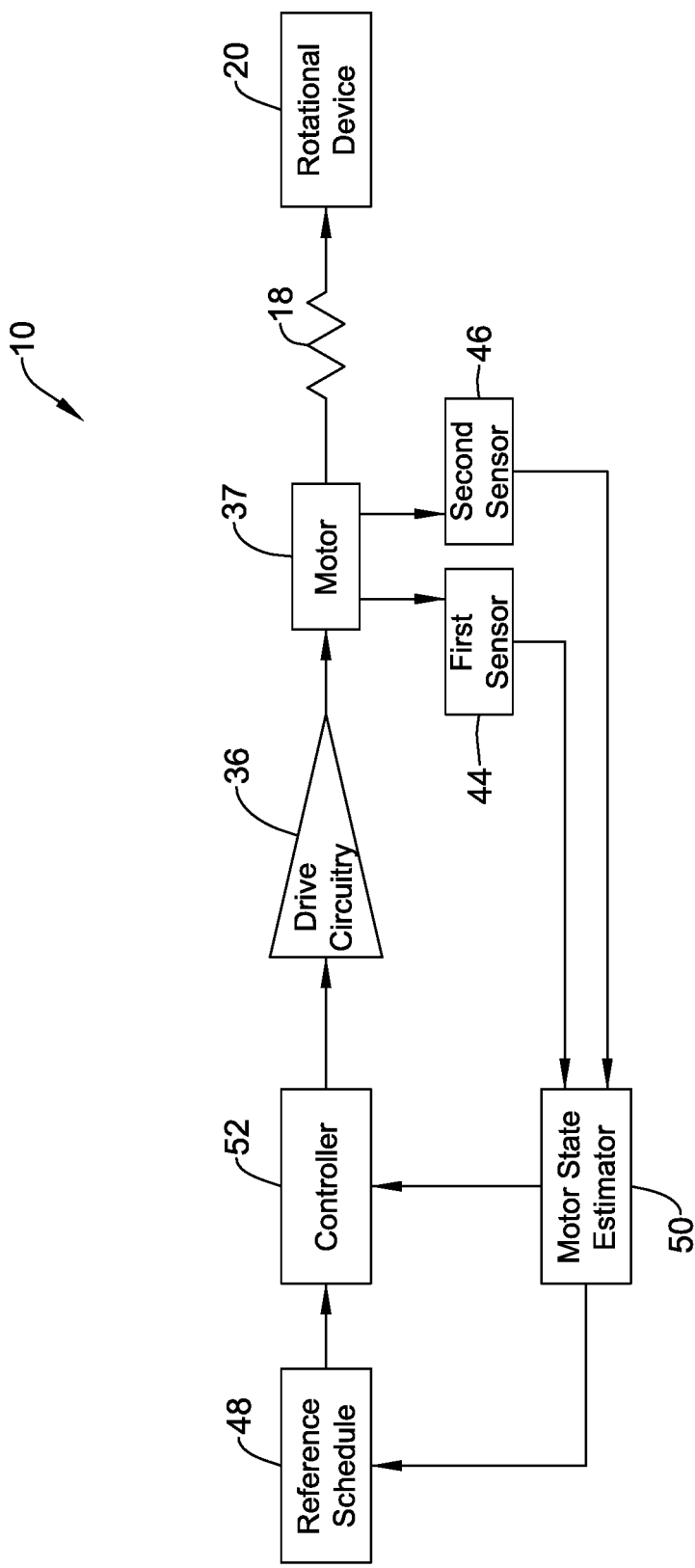
FIG. 3 is a schematic flow diagram of an example atherectomy system.

FIG. 3 depicts a schematic block diagram of control software and circuitry of the atherectomy system 10 coupled with the motor 37, which in turn is operatively attached to the drive shaft 18 and the rotational device 20. The control software and circuitry may include, among other features, the drive circuitry 36 (when included), a reference schedule component 48, a motor state estimator 50 (e.g., a motor state observer or other motor state estimator), and a controller 52 (e.g., a feedback controller, a closed loop controller or feedback regulator, such as a proportional-integral-derivative (PID) controller or other controller). Although the reference schedule component 48, the motor state estimator 50, and the controller 52 are depicted as being separate components in FIG. 3, one or more of the reference schedule component 48, the motor state estimator 50, and the controller 52 may be implemented in a single controller or processor or, alternatively, multiple controllers or processors that may be configured to perform the functions of the disclosed reference schedule component 48, motor state estimator 50, and the controller 52. Although not necessarily required, one or more of the reference schedule component 48, the motor state estimator 50, the controller 52, the drive circuitry 36, and/or other electronic processing components of the atherectomy system 10 may be implemented on the processor 38, the memory 40, and/or the input/output port 42 (e.g., the processor 38, the memory 40, and/or the input/output port 42 may be configured to effect operation of one or more of the reference schedule component 48, the motor state estimator 50, the controller 52, the drive circuitry 36, and/or other electronic processing components of the atherectomy system 10).

The reference schedule component 48 may include a reference schedule that relates a motor state to a motor input or set point (e.g., a reference value) for a motor state. That is, for any possible value of a motor state, the reference schedule may have a related reference value (e.g., a motor input or set point for a motor state). Example motor states may include, but are not limited to, motor speed, motor position, motor torque, motor drive current, motor drive voltage, motor drive electric power, and/or other motor states. An example reference schedule may relate speed to torque, speed to electric current, speed to electric voltage, and/or may relate one or more other motor states to a reference motor state. For example, a control system utilizing the reference schedule that relates speed to torque may receive a speed input (e.g., from a motor state estimator or other component of the atherectomy system 10) and provide a reference torque (e.g., for use the by the controller 52 or other component of the atherectomy system 10) on which a control signal may be based.

In some cases, the reference schedule of the reference schedule component 48 may be saved in memory 40 and/or other memory and accessed or otherwise utilized by the processor 38 to determine a reference value based on an input (e.g., an input motor state, such as speed). The reference schedule component 48 may be or may include the memory 40, but this is not required.

The reference schedule may be predetermined before operation of the atherectomy device (e.g., during calibration or pre-set by a manufacturer) and saved in the memory 40 or other memory. In some cases, a user may be able to adjust or otherwise modify the reference schedule and save it in the memory 40 or other memory to establish a predetermined or off-line reference schedule. The reference schedule may be considered predetermined or off-line if it is not modified in real-time during operation of the drive assembly 12.

The motor state estimator 50 may be configured to estimate one or more states of the motor 37 based on inputs received from sensors sensing motor parameters (e.g., where sensed motor parameters may be measured motor states). Example motor parameters may include drive current, drive voltage, input power, motor position, etc. In one case, the first sensor 44 may sense an input current to the motor 37 and provide signals indicative of a value of motor drive current or other electrical input to the motor state estimator 50. Additionally, or alternatively, the second sensor 46 may sense a position of the motor 37 and provide signals indicative of a position value of the motor 37 to the motor state estimator 50. In some cases, a sensor configured to sense a position of a motor may be a Hall-effect sensor, but other position sensors may be additionally or alternatively be utilized. Although sensors 44, 46 are disclosed as sensing current and motor position, these sensors may be configured to sense additional or alternative other parameters and/or other sensors may be included in the atherectomy system 10 that sense similar or different motor parameters.

Based on sensed values of motor parameters provided to the motor state estimator 50, the motor state estimator 50 may calculate (e.g., estimate) one or more motor states. In one example, based on received values indicative of motor position, timing of position values, and known relationships of motor position and time, the motor state estimator 50 may calculate or determine (e.g., estimate) a speed (e.g., RPMs or other speed parameter) of the motor 37. In another example, based on received values indicative of motor position, received values indicative of drive current or other electrical input, and known relationships of motor position to electrical input to a motor, the motor state estimator 50 may calculate or determine (e.g., estimate) a torque of the motor 37. Other motor states may be determined by the motor state estimator 50.

The controller 52 or other controller may be configured to provide control signals to the drive circuitry 36 (when included) and/or to the motor 37. In some cases, the controller 52 or other controller may receive a reference value based on a motor parameter from the reference schedule component 48 and a calculated or determined current value of a motor state from the motor state estimator 50. Based on comparing the reference value to the calculated or determined value, the controller 52 or other controller determines a control signal for maintaining or adjusting an operation of the motor 37. In some cases, when a large delta occurs between the reference value and the calculated or determined value or a threshold value is reached (as discussed in greater detail below), the controller 52 may send a signal to the drive circuitry 36 and/or the motor 37 to actively brake the motor 37 (e.g., reverse a direction of current provided to the motor 37 or torque on the motor 37). In some cases, the motor may be actively braked until it stops rotating. Controllers in addition to or other than the controller 52 that are configured to determine a motor control signal based on a reference value of a parameter compared to a measured, determined, or calculated real time value of the parameter may be utilized.

Along with feedback from the first sensor 44, the second sensor 46, and/or other sensors, the reference schedule component 48, the motor state estimator 50, and the controller 52 or other system with a functionally similar configuration may facilitate a closed loop control of the motor 37 and the rotational device 20 based on the feedback from the sensors (e.g., the first sensor 44 and the second sensor 46) and a reference schedule of the reference schedule component 48. This closed loop control of the motor 37 and the rotational device 20 may allow active deceleration of the motor 37 upon detection or identification of a stall condition, which facilitates using the atherectomy system 10 in a safe manner while maintaining a maximum torque at the rotational device 20 to provide effective therapy in a desirable amount of time. Moreover, the closed loop control configuration may allow continuous monitoring for jam or stall conditions, early identification of jam or stall conditions, and implementation of pro-active steps (e.g., active braking of the motor 37, etc.) to mitigate forces acting on a patient when the jam or stall occurs.

Figure 4:
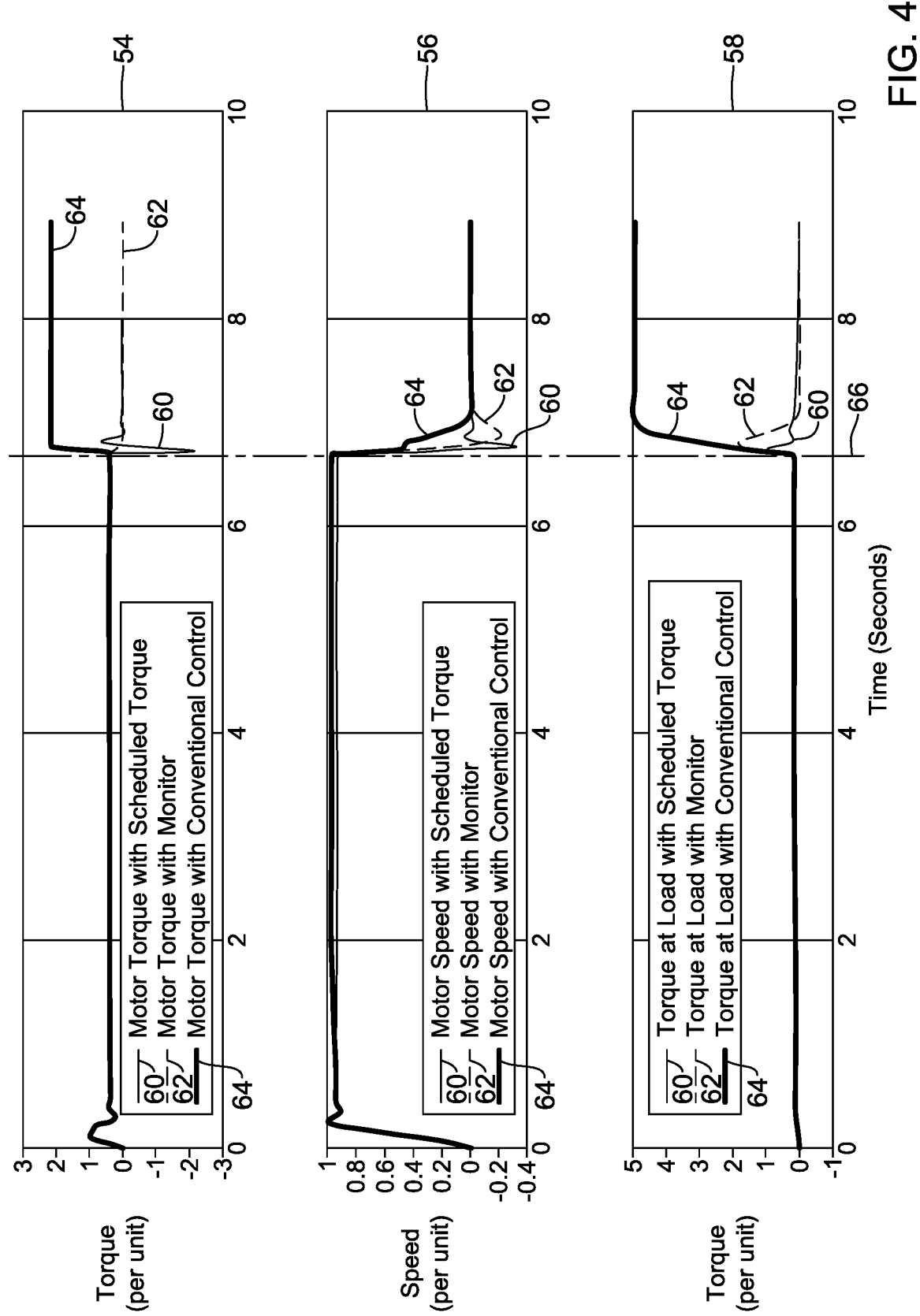
FIG. 4 depicts graphs showing operations of three atherectomy systems, each atherectomy system having a different control approach.

FIG. 4 shows three graphs on the same time scale in seconds that depict how three different atherectomy systems respond to a jam or stall at a respective rotational device (e.g., when the rotational device 20 stops moving due to an obstruction). As shown in FIG. 4, graph 54 depicts motor torque over time, graph 56 depicts motor speed over time, and graph 58 depicts torque at a rotational device (e.g., at a load) over time.

In the graphs of FIG. 4, lines 60, 62, and 64 represent different atherectomy systems. Line 60 represents operation of the atherectomy system 10 described herein and that utilizes the disclosed reference schedule configuration for automatically identifying and addressing a jam or stall condition. Line 62 (e.g., the broken line) represents an atherectomy system in which the system is monitored for a jam or stall condition and addresses a detected jam or stall condition by removing power to a motor and allowing the power to rotate freely until any built up torque in the system has dissipated. Line 64 (e.g., the bolded line) represents a conventional atherectomy system that does not include automatically monitoring for a jam or stall condition and addressing any identified jam or stall condition, but instead relies on a user to stop the motor of the atherectomy system after a jam or stall occurs.

In the nine (9) second time history of operation of the three different atherectomy systems depicted in the graphs FIG. 4, the respective motors begin from a dead stop at time equal to zero (0) and are then turned on. After reaching full speed for about six (6) seconds, at line 66 it can be seen that the respective rotational devices are jammed and are stopped nearly instantaneously. Such an instantaneous or nearly instantaneous stop of the rotational devices may cause the respective drive shafts to act like a large spring that is fixed on one end (e.g., the end at which the rotational device is jammed) with the motor behaving as a combination of a mass and damper at the other end. After a jam occurs, the atherectomy system represented by line 64 continues to drive the motor resulting in force from motor torque and kinetic energy both being fed into the drive cable and resulting in an increase torque on the motor (graph 54) and an increase in torque on the rotational device (graph 58). After a jam occurs, the atherectomy system represented by line 62 stops rotating the motor and thus, stops introducing torque into the system, but all of the kinetic energy already in the system is still transferred to the jammed rotational device, which results in a torque spike at the rotational device, as is shown in graph 58. After a jam or stall condition is identified, the atherectomy system 10 disclosed herein and represented by line 60 brakes the motor (e.g., the motor 37) and effectively throws away a portion of the system's kinetic energy. As the atherectomy system 10 transfers less force to a patient via the rotational device when a jam occurs or is identified than conventional atherectomy systems in which there is no monitoring of jams or an automated response to jams and the atherectomy system which automatically release a motor when a jam is detected, the atherectomy system 10 provides an improvement over existing techniques for addressing jams and/or stall conditions of an atherectomy system.

Figure 5:
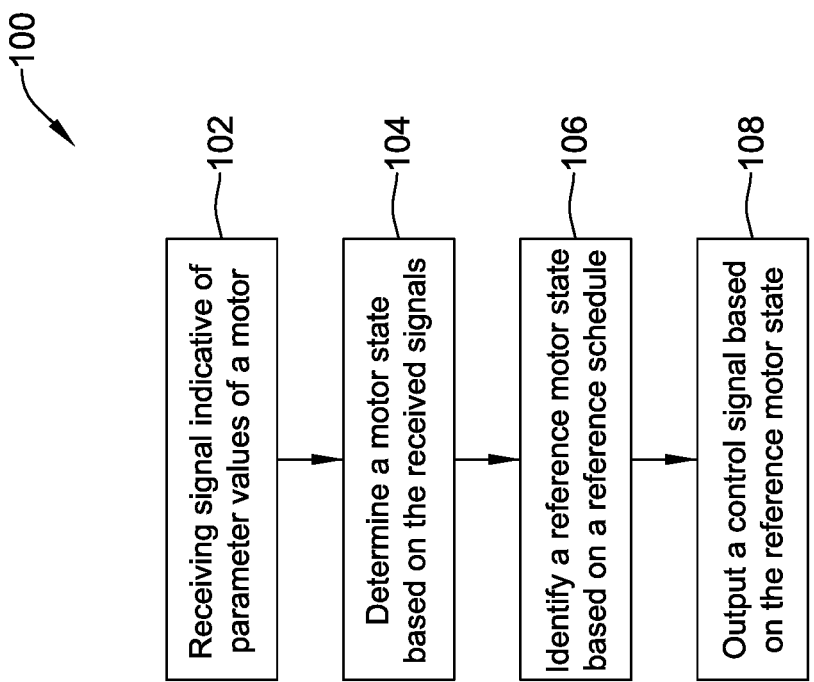
FIG. 5 is a schematic flow diagram of an example method of operating an atherectomy system.

FIG. 5 depicts a flow diagram of a method 100 of controlling an atherectomy system (e.g., the atherectomy system 10 or other atherectomy system) in an automated manner that facilitates detecting a stall condition or jam in the rotational device (e.g., the rotational device 20 or other rotational device) and in response decelerating a motor (e.g., the motor 37 or other motor) to mitigate forces applied to a patient if the stall or jam occurs. In the method 100, one or more motor states of the motor may be monitored based on values from sensors sensing motor parameters including, but not limited to, drive current, drive voltage, motor position, etc.

Turning to the method 100, signals indicative of parameter values of a motor may be received 102, as shown in FIG. 5. The parameter values of a motor may be sensed by one or more sensors (e.g., the first sensor 44, the second sensor 46, and/or other sensor) and signals indicative of the sensed parameter values may be sent from the sensors to a controller (e.g., the control unit 14 having a motor state estimator 50 or other controller). Example sensed parameter values include, but are not limited to, drive current for the motor, drive voltage to the motor, motor position, and so on. The controller may use the signals indicative of the sensed parameter values to determine 104 one or more motor states of the monitored motor using known relationships (e.g., equations) between sensed parameter values and motor states. Example motor states include, but are not limited to, real time motor speed, real time motor torque, real time drive current, real time drive voltage, real time drive power, and so on. Values and/or motor states taken or determined in real time may be considered to be taken or determined during operation of the atherectomy system.

The controller may then identify 106 a reference motor state or a reference motor input based on a determined motor state. In one example, the controller may identify 106 a reference motor state based on a determined motor speed. Then, based on the reference motor state (e.g., based directly on the reference motor state and/or a comparison of the reference motor state to the determined motor state), the controller may output 108 a control signal based on the reference motor state or reference motor input. In some cases, the control signal outputted from the control unit (e.g., the control unit 14 or other control unit) may be a control signal to decelerate the motor to stop the motor after a jam or stall condition has been detected. The control signal may result in reversing a direction of torque on the motor, reversing a direction of current provided to the motor, reducing an amount of voltage provided to the motor, reversing a direction of current provided to the motor, and/or result in one or more other effects on a motor state of the motor to decelerate the motor in response to detecting a jam or stall condition. In one example, the jam or stall condition may be detected when the determined motor state (e.g., speed or other motor state) reaches or goes beyond a threshold value, as will be discussed in greater detail with respect to FIGS. 6-8.

Further, in some cases, controlling the atherectomy system may include identifying a first motor state and a second motor state, where the first motor state (e.g., speed) may be utilized to determine a reference motor state and the determined second motor state (e.g., torque) may be compared to the reference motor state. In such instances, the controller may output the control signal to maintain or change operation of the motor based on the reference motor state and the determined current motor state.

The controller or other monitoring component may continually monitor for a jam or stall condition during operation of the atherectomy system using the method 100 and/or other techniques disclosed herein. In one example, the controller may continually repeat the steps of the method 100 and/or repeat the steps of the method 100 at predetermined intervals during operation of the motor of the atherectomy system to monitor for a jam or stall condition occurring at the rotational device of the atherectomy system.

Figure 6:
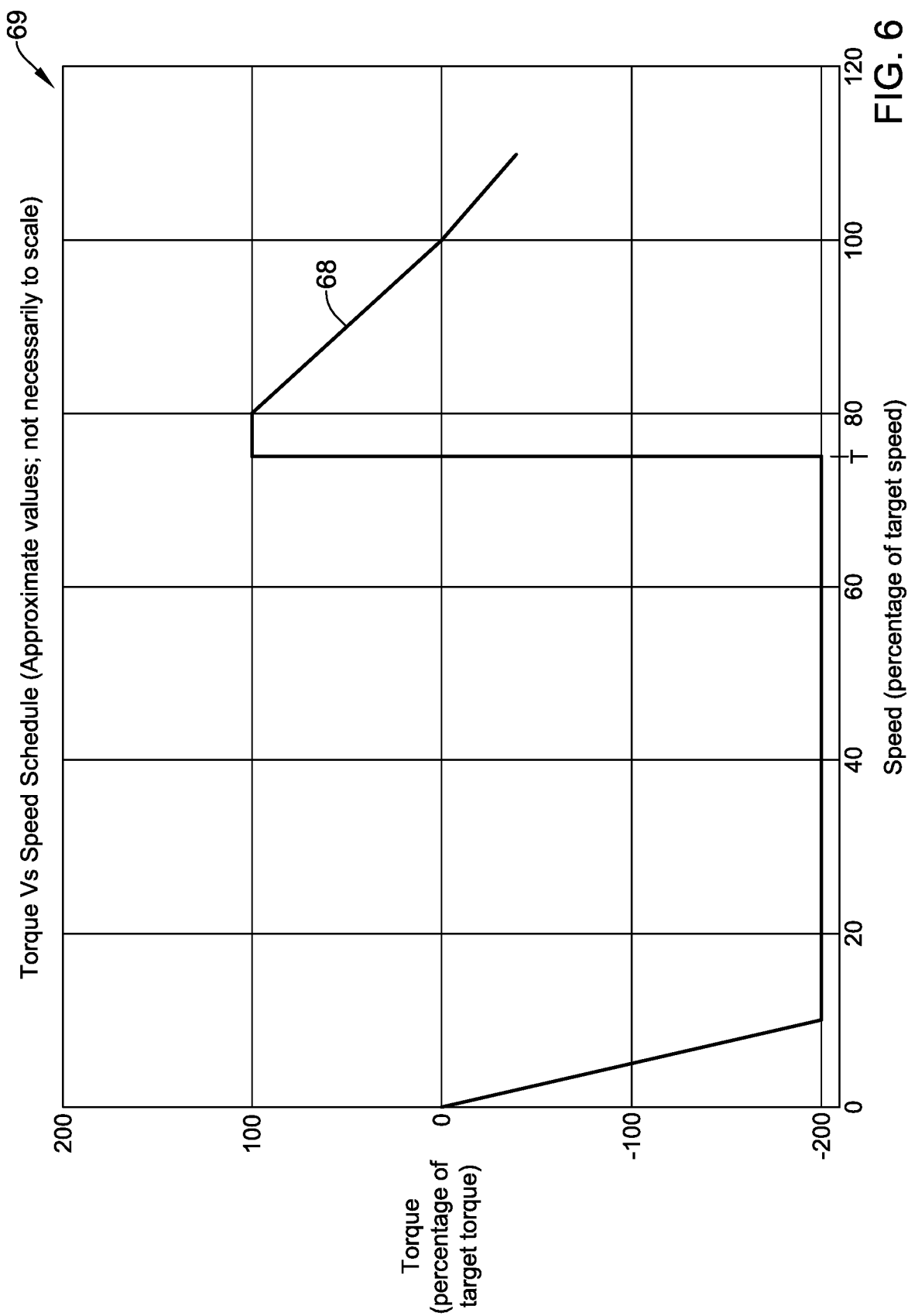
FIG. 6 is an example reference schedule of motor speed versus motor torque for an atherectomy system.
Figure 7:
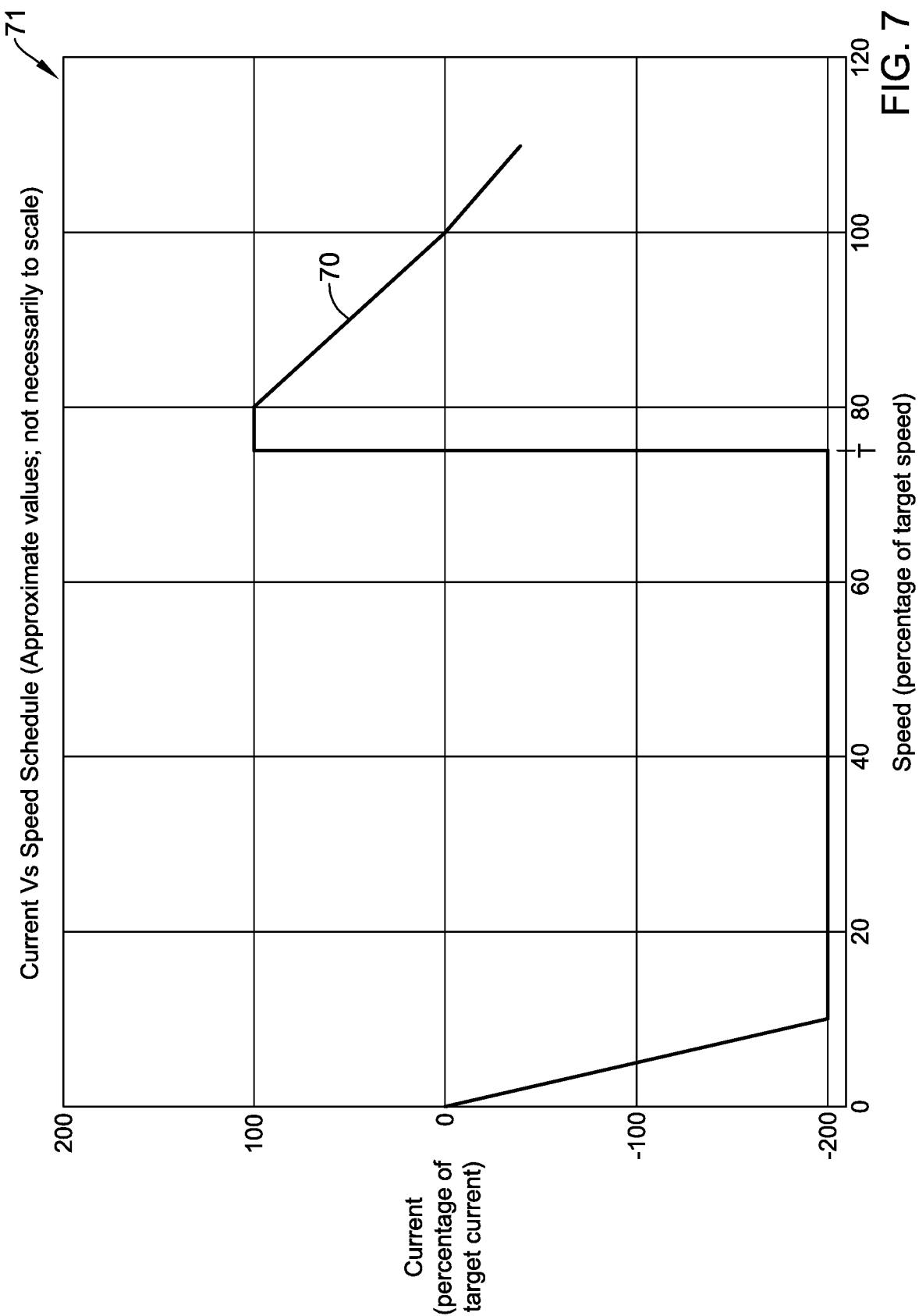
FIG. 7 is an example reference schedule of motor speed versus drive current for an atherectomy system.

FIGS. 6-8 depict illustrative reference schedules for the reference schedule component 48 that the atherectomy system 10 may follow to identify a jam or stall condition and address the jam or stall condition. FIG. 6 depicts line 68 of a reference schedule 69 that compares motor torque to motor speed, where torque is measured as a percentage of a target motor torque and speed is measured as a percentage of a target motor speed. FIG. 7 depicts line 70 of a reference schedule 71 that compares drive current for a motor to motor speed, where drive current provided to the motor is measured as a percentage of a target current for a motor and speed is measured as a percentage of a motor speed. FIG. 8 depicts lines 72 and 74 of a reference schedule 75 that compares drive voltage for a motor to motor speed, where drive voltage to the motor is measured as a percentage of a target drive voltage for a motor and speed is measured as a percentage of a motor speed.

Although FIGS. 6-8 depict reference schedules as taking the form of a graph, the reference schedules may have other forms. Example forms of reference schedules include, but are not limited to graphs, equations, look-up tables, and so on. It is noted that utilizing look-up tables or graphs for a reference schedule may reduce processing power needed during operation of the atherectomy system 10 when compared to the processing power needed during operation of the atherectomy system 10 that follows a reference schedule represented by an equation.

Once the determined speed or other determined motor state reaches or goes beyond a threshold value (e.g., speed value T in FIGS. 6-8), the control system may automatically modify operation of the atherectomy system 10 and indicate on a display or otherwise indicate, through a visual alarm, through an audible alarm, or through one or more other mechanisms, that a jam or stall condition has been detected and addressed. In some cases, no indication of a jam or stall condition is provided other than automatically decelerating the motor of the atherectomy system 10.

As shown in FIGS. 6-8, the threshold speed value has been set at 75% of a target speed. However, a threshold value of a reference schedule may be a different percentage of a target speed, may be a different speed value, and/or may be a threshold of a different motor state or motor parameter than speed. Further, the threshold value may vary based on a setting or other state of the atherectomy system 10. For example, an atherectomy system 10 may include a plurality of speed settings (e.g., a first setting having a first maximum speed and a second setting having a second maximum speed) and each setting may have a different threshold value associated with two or more of the settings. Using the threshold value may facilitate, among other benefits, detecting the jam or stall condition before the jam or the stall actually occur, but this is not required.

There are several points that may be noted, some of which are discussed below, when viewing the reference schedules of FIGS. 6-8. First, when the target RPM of a motor is at a target RPM, the torque value, the current value, and a difference between a target voltage (e.g., a scheduled root mean square (RMS) voltage value) and a back electromotive force (EMF) is at or near zero (0), as depicted respectively in FIGS. 6-8. Second, as the motor's speed reaches and/or goes beyond a threshold value, the torque value, current value, and the difference between the back EMF voltage and the target voltage may rapidly transition from positive to negative, as depicted respectively in FIGS. 6-8. Third, although the figures generally show flat lines 68, 70, and 72 (e.g., based on linear functions in some cases), the reference schedules may actually be based on quadratic functions and/or other non-linear functions to obtain the desired performance when controlling the atherectomy system 10 in the manner described herein.

In one example method of controlling an atherectomy system 10, the reference schedule 69 of FIG. 6 may be followed and the following steps may be repeated over time until a jam or stall condition is identified. To begin, a real time or instantaneous torque on the motor 37 may be identified. The real time or instantaneous torque on the motor 37 may be based on a measured motor state and a measured motor drive state. For example, the real time or instantaneous torque on the motor may be calculated or determined using a measured or sensed drive power (e.g., drive current) and/or production parameters of the motor 37. Then, the real time or instantaneous motor speed may be determined based on the measured or sensed motor position and a reference motor torque may be identified from the determined real time or instantaneous motor speed and line 68 in the reference schedule 69 in FIG. 6. A control signal for the motor 37 may then be generated by a controller based on the reference motor torque and the real time or instantaneous torque. In one example, if the real time or instantaneous speed has not reached or gone beyond a threshold speed value T (e.g., to the right of the threshold value T in FIG. 6), the reference torque may be similar to the real time or instantaneous torque and the controller may issue a control signal to the motor based on the differences between the reference torque and the real time or instantaneous torque to maintain operation and/or make slight modifications (e.g., damping, corrective, and/or other modifications). However, if the real time or instantaneous speed has reached or gone beyond the threshold value T (e.g., at or to the left of the threshold speed value T in FIG. 6), the reference torque will be substantially different than the determined real time or instantaneous torque and the controller will output a control signal based on the difference between the reference torque and the real time or instantaneous torque to brake the motor and mitigate forces applied to a patient as a speed of a motor is reduced. In the example of FIG. 6, the control signal may reverse the motor torque to decelerate the motor until the motor speed is at or about zero (0).

In a further example method of controlling an atherectomy system 10, the reference schedule 71 of FIG. 7 may be followed and the following steps may be repeated over time until a jam or stall condition is identified. To begin, a real time or instantaneous drive current to the motor 37 may be identified. The real time or instantaneous drive current to the motor 37 may be based on a measured motor state and a measured motor drive state (e.g., measured motor parameters). Then, the real time or instantaneous motor speed may be determined based on the measured or sensed motor position and a reference drive current for a motor may be identified from the determined real time or instantaneous motor speed and line 70 in the reference schedule 71 in FIG. 7. A control signal for the motor 37 may then be generated by a controller based on the reference drive current and the real time or instantaneous current. In an example, if the real time or instantaneous speed has not reached or gone beyond a threshold value T (e.g., to the right of the threshold speed value T in FIG. 7), the reference drive current may be similar to the real time or instantaneous drive current and the controller may issue a control signal to the motor based on the differences between the reference drive current and the real time or instantaneous drive current to maintain operation and/or make slight modifications (e.g., damping, corrective, and/or other modifications). However, if the real time or instantaneous speed has reached or gone beyond the threshold speed value T (e.g., at or to the left of the threshold value T in FIG. 7), the reference drive current will be substantially different than the determined real time or instantaneous drive current and the controller will output a control signal based on the difference between the reference drive current and the real time or instantaneous drive current to brake the motor and mitigate forces applied to a patient as a speed of a motor is reduced. In the example of FIG. 7, the control signal may reverse the direction of the drive current to decelerate the motor until the motor speed is at or about zero (0).

In a further example method of controlling an atherectomy system 10, the reference schedule 75 of FIG. 8 may be followed and the following steps may be repeated over time until a jam or stall condition is identified. To begin, a real time or instantaneous back EMF may be identified. The real time or instantaneous back EMF of the motor 37 may be based on a measured motor state and a measured motor drive state. For example, the real time or instantaneous back EMF may be calculated using the known voltage, motor position, and/or production parameters of the motor. Then, the real time or instantaneous RMS voltage may be determined or estimated based on a measured motor drive state (e.g., a measured motor parameter). For example, the real time or instantaneous RMS voltage may be determined or estimated from a known voltage from a power supply to the motor combined with a known pulse width modulation (PWM) duty cycle. Then, the real time or instantaneous motor speed may be determined based on the measured or sensed motor position and a reference voltage for a motor may be identified from the determined real time or instantaneous motor speed, back EMF, and line 72 in the reference schedule 75 in FIG. 8. A control signal for the motor 37 may then be generated by a controller based on the reference voltage and the real time or instantaneous RMS voltage. In one example, if the real time or instantaneous speed has not reached or gone beyond a threshold value T (e.g., to the right of the threshold speed value T in FIG. 8), the reference voltage may be similar to the real time or instantaneous RMS voltage and the controller may issue a control signal to the motor based on the differences between the reference voltage and the real time or instantaneous RMS voltage to maintain operation and/or make slight modifications (e.g., damping, corrective, and/or other modifications). However, if the real time or instantaneous speed has reached or gone beyond the threshold speed value T (e.g., at or to the left of the threshold value T in FIG. 8), the reference voltage will be substantially different than the determined real time or instantaneous RMS voltage and the controller will output a control signal based on the difference between the reference voltage and the real time or instantaneous RMS voltage to brake the motor and mitigate forces applied to a patient as a speed of a motor is reduced. In the example of FIG. 8, the control signal may reduce the motor voltage to decelerate the motor until the motor speed is at or about zero (0).

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A medical device configured for use in an atherectomy procedure in a vessel of a patient, the medical device comprising:
   an elongated drive shaft;
   a rotational tip member coupled to a distal end of the elongated drive shaft, the rotational tip member configured to rotate and engage material in a patient vessel while rotating;
   a motor coupled to a proximal end of the elongated drive shaft to rotate the rotational tip member; and
   a control unit configured to control a motor state of the motor, the control unit is further configured to adjust the motor state to decelerate the motor in response to a detected stall condition, and
   wherein the stall condition is detected when a speed of the motor reaches or goes beyond a threshold level.

2. The medical device of claim 1, wherein: the motor state is a torque on the motor.

3. The medical device of claim 2, wherein adjusting the torque on the motor includes reversing a direction of torque on the motor.

4. The medical device of claim 1, wherein the control unit is configured to adjust the motor state of the motor by reversing a direction of current provided to the motor to decelerate the motor in response to the detected stall condition.

5. The medical device of claim 1, wherein the control unit is configured to adjust the motor state of the motor by reducing an amount of voltage provided to the motor to decelerate the motor in response to the detected stall condition.

6. The medical device of claim 1, wherein the control unit is configured to adjust the motor state of the motor based on a predetermined motor speed reference schedule and motor parameters received by the control unit during operation of the motor.

7. The medical device of claim 6, wherein the motor parameters include a measurement of current provided to the motor and a measurement of a rotational position of the motor.

8. The medical device of claim 1, further comprising:
   a first sensor sensing a current provided to the motor; and
   a second sensor sensing a position of the motor; and
   wherein the first sensor provides a signal indicative of a sensed current to the control unit and the second sensor provides a signal indicative of a sensed position to the control unit.

9. The medical device of claim 8, wherein:
   the control unit is configured to determine a speed of the motor based on the signal indicative of a sensed position of the motor; and
   the control unit is configured to determine the motor state of the motor based on the signal indicative of a sensed current and the signal indicative of a sensed position, the determined motor state is a motor state other than the determined speed of the motor.

10. The medical device of claim 9, wherein the control unit is configured to:
    determine a reference motor state based on the speed of the motor and compare the determined reference motor state to the determined motor state; and
    issue a command signal for the motor based on the comparison between the reference motor state to the determined motor state.

11. A control unit for controlling a medical device during an atherectomy procedure in a patient's vessel, the control unit comprising:
    a controller;
    a motor state estimator in communication with the controller; and
    a reference schedule component in communication with the controller and the motor state estimator, the reference schedule component is configured to provide an output to the controller based on an input from the motor state estimator and the input from the motor state estimator includes a motor speed;
    wherein the controller is configured to output a control signal for decelerating a motor in communication with a distal rotational tip member configured to rotationally engage material in a patient's vessel during an atherectomy procedure based on the output received from the reference schedule component, and
    wherein controller is configured to output the control signal for decelerating the motor when the motor speed reaches or goes beyond a threshold level.

12. The control unit of claim 11, wherein the reference schedule component is configured to provide a reference motor state based on the motor speed.

13. The control unit of claim 11, wherein:
    the motor state estimator is configured to receive signals indicative of sensed motor parameters and provide an output to the controller based on the received signals indicative of sensed motor parameters; and
    the outputted control signal is based on the output from the motor state estimator to the controller.

14. The control unit of claim 13, wherein:
    the output from the reference schedule component to the controller is a reference motor state and the output from the motor state estimator to the controller is a real time motor state; and
    the controller is configured to determine the control signal based on a difference between the reference motor state and a real time motor state.

15. The control unit of claim 14, wherein the reference motor state is a reference torque for the motor and the real time motor state is a real time torque of the motor.

16. The control unit of claim 11, further comprising:
    a processor;
    memory in communication with the processor; and
    an input/output port in communication with the processor; and
    wherein the processor and the memory are configured to effect operation of the controller and the reference schedule component to output the control signal via the input/output port.

17. A method of controlling a medical device during an atherectomy procedure in a patient's vessel, the method comprising:
    receiving signals indicative of a sensed position of a motor, the motor is operational to rotate a distal rotational tip member configured to engage material in a patient's vessel during an atherectomy procedure;
    determining a speed of the motor based on the signals indicative of a sensed position of the motor;
    identifying a reference motor state based on the determined speed of the motor and a predetermined reference schedule; and
    outputting a control signal to the motor to decelerate the motor, the outputted control signal is based on the reference motor state, and wherein the control signal to decelerate the motor is outputted to the motor when the determined speed of the motor reaches or goes beyond a threshold level.

18. The method of claim 17, further comprising:
receiving signals indicative of a sensed current provided to the motor;
determining a real time motor state based on the received signals indicative of a sensed motor parameter and the received signals indicative of a sensed current;
wherein the outputted control signal is based on the real time motor state.

19. The method of claim 18, wherein the reference motor state is a reference motor torque and the real time motor state is a real time motor torque.

\* \* \* \* \*